United States Patent [19]
Ovadia et al.

[11] 4,087,534
[45] May 2, 1978

[54] N-HALOALKYLMIO URAZOLE PESTICIDES

[76] Inventors: David Ovadia, 59 Hazvi Street; Nitzah Peleg, 703 Hanesiim Street, both of Beer Sheva; Peretz Bracha, 14 Tamar Street, Omer, all of Israel

[21] Appl. No.: 767,884

[22] Filed: Feb. 11, 1977

Related U.S. Application Data

[63] Continuation-in-part of Ser. No. 579,007, May 19, 1975, abandoned.

[30] Foreign Application Priority Data

May 22, 1974 Israel ........................................ 44882

[51] Int. Cl.² ...................... A01N 9/12; A61K 31/41; C07D 249/12
[52] U.S. Cl. ................................ 424/269; 260/308 C
[58] Field of Search ..................... 260/308 C; 424/269

[56] References Cited

U.S. PATENT DOCUMENTS

| 2,553,770 | 5/1951 | Kittleson .............................. 260/301 |
| 2,856,410 | 10/1958 | Kittleson et al. ..................... 260/301 |
| 3,484,451 | 12/1969 | Moon .................................. 260/308 C |

OTHER PUBLICATIONS

Matolcsy et al., Chem. Abstracts, vol. 72, Abstract No. 100656y (1970).

*Primary Examiner*—Alton D. Rollins
*Attorney, Agent, or Firm*—Browdy and Neimark

[57] ABSTRACT

Novel haloalkylthio 4-substituted urazoles and thiourazoles of the formula:

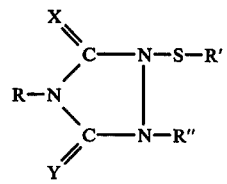

wherein
R is alkyl of 1–12 carbon atoms, cycloalkyl having 3–6 carbon atoms, lower monohaloalkyl, benzyl, phenylethyl and phenyl optionally substituted by 1–3 halogens, nitro, chloromethyl, trifluoromethyl, lower alkyl, lower alkoxy or lower thioalkyl groups;
R' designates haloalkyl of 1 or 2 carbon atoms, having at least two halogen atoms, and
R" designates R or —SR', and X and Y each designate independently oxygen or sulfur:
a process for preparing the above defined novel compounds, and fungistatic, fungicidal, bacteriostatic and bactericidal compositions of matter containing such compounds as active ingredient.

15 Claims, No Drawings

N-HALOALKYLMIO URAZOLE PESTICIDES

This is a continuation-in-part of our copending application Ser. No. 597,007 filed May 19, 1975, now abandoned.

BACKGROUND OF THE INVENTION

This invention pertains to novel organic chemical compounds and to their preparation, to new biocidal compositions, and to a novel method for controlling microbes. The present invention is more particularly directed to new (1-and-2-)haloalkylthio urazoles and thiourazoles, to new microbiocidal compositions containing the same, and to their use in controlling microbes such as fungi and bacteria.

STATE OF THE PRIOR ART

Urazoles and their derivatives are known to possess medicinal and microbiocidal properties. For example, J. Bourdais et.al. Bull. Soc. Chim. France (1964)500; (C.A.,61: 3094h)/ and German patent 1,200,313 (C.A.: 64 : 3556g) describe the synthesis of some urazoles and their use in pharmaceutical preparations. It is also known that compounds containing an >NSCCl$_3$ group, as described in US 2,553,770 and US 2,875,030 are excellent fungicides. Recently Matolosy and Bordas /Acta. Phytopathol., 4(1969) 197(C.A.,75: 100656y)/ and U.S. Pat. No. 3,484,451 described certain 4-(trichloromethylthio) urazoles and their anti-fungal activity. These references disclose hetercyclic compounds having an >NSCCl$_3$ group linked to either two carbon atoms, two acyl groups or one acylgroup and one carbon atom. Thiourazoles are also known and have been reported by Abbasi and Trivedi (J. Ind. Chem. Soc., 42(1965)333; C.A.,63: 6997f).

SUMMARY OF THE INVENTION

According to the present invention there is provided a novel class of 4-substituted urazoles and thiourazoles having at least one haloalkylthio substituent on a hydrazine nitrogen atom of the ring. The novel haloalkylthio 4-substituted urazoles and thiourazoles are represented by the following formula:

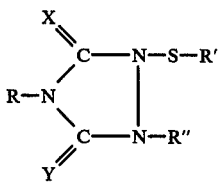

wherein
R is alkyl of 1-12 carbon atoms, cycloalkyl having 3-6 carbon atoms, lower monohaloalkyl, benzyl, phenylethyl and phenyl optionally substituted by 1-3 halogens, nitro, chloromethyl, trifluoromethyl, lower alkyl, lower alkoxy or lower thioalkyl groups;
R' is a haloalkyl group having 1 to 2 carbon atoms and at least 2 halogen substituents;
R" is R — or — SR'; and X and Y are independently oxygen or sulfur.
Preferred compounds are those where R is lower alkyl having 1-4 carbon atoms, cyclohexyl and phenyl optionally substituted by 1 to 2 halogens, preferably chlorine.
Another preferred group of compounds are those where R" is equal to — SR'. Most preferred are the urazole derivatives where both X and Y are oxygen. Examples of R — falling within the scope of the invention are methyl, ethyl, propyl, isopropyl, butyl, pentyl, hexyl, heptyl, octyl, nonyl, decyl, undecyl, dodecyl and the respective isomeric forms of these, cyclopropyl, cyclobutyl, cyclopentyl, cyclohexyl, chloromethyl, chloroethyl, chloropropyl, chlorobutyl, bromoethyl, bromobutyl, phenyl, benzyl, phenylethyl, 3-chlorophenyl, 4-chlorophenyl, 3,4-dichlorophenyl, 4-bromophenyl, 4-nitrophenyl, 3,4-dinitrophenyl, 4-methylphenyl, 4-ethylphenyl, 4-propylphenyl, 4-methoxyphenyl, 3-ethoxyphenyl, 4-methylthiophenyl, 3-ethylthiophenyl or trifluoromethylphenyl.

Examples of haloalkyl groups of 1 to 2 carbon atoms falling within the invention are bromochlorofluoromethyl, bromodichloromethyl, chlorodifluoromethyl, dichloromethyl, fluorodichloromethyl, 1-fluoro-1,1,2,2-tetrachloroethyl, 1,1,2,2-tetrachlethyl, 2,2,2-trichloroethyl, 1,2,2-trichloroethyl, trichloromethyl and the like. A preferred group is one having at least 3 halogens; and most preferred is the chloroalkyl group.

The new haloalkylthio 4-substituted urazoles and thiourazoles of this invention may be prepared by reacting a haloalkylsulfenyl halide with an alkali metal salt of a 4-substituted urazole or thiourazole. The reaction is advantageously effected in an aqueous medium, preferably an aqueous solution of an alkali metal hydroxide (e.g., sodium or potassium hydroxide), so as to form the alkali metal salt of the 4-substituted urazole or thiourazole in-situ. A pre-formed alkali metal salt of the 4-substituted urazole, or thiourazole can also be used if desired. Heat is evolved by the reaction of the alkali metal urazole or thiourazole salt with the haloalkylsulfenyl halide, so that the reactants should be mixed slowly, accompanied by thorough stirring. The temperature of the reaction mixture is preferably kept at about 0° C., but reaction temperature as low as about −10° C and as high as about 30° C can be used. At the higher temperatures the reactants should be mixed slowly. The reaction products separate from the reaction mixture as solids.

The stoichiometry of the reaction requires one or two molecular equivalents of the haloalkylsulfenyl halide for each mole of 4-substituted urazole or thiourazole depending upon the number of hydrogens on the urazole being replaced. In either case, however, a slight molar excess of the haloalkylsulfenyl halide is prefered, although an excess of either reactant can be used if desired.

The new 4-substituted -2-(haloalkylthio)- and 4-substituted -1, 2-bis-(haloalkylthio) urazoles and thiourazoles are recovered from the reaction mixture and purified by conventional methods. When the desired product separates as a solid from the reaction mixture, it can be filtered, washed free of by-products and unreacted starting materials, and recrystallized from a suitable solvent, e.g., petroleum ether, benzene, cyclohexane, and the like.

4-Substituted urazole starting materials can be prepared according to known methods. Illustratively, they can be prepared by heating and cyclizing 4-substituted-1-carbethoxysemicarbazides in the presence of aqueous base according to the method of Cookson et.al., Organic Syntheses, 51(1971)121. The starting 1-carbethoxysemicarbazides may be prepared by condensing diethyl hydrazine carboxylate with an isocyanate according to the above method of Cookson.

The novel 4-substituted haloalkylthio urazoles or thiourazoles of this invention can be used as active ingredients of fungicidal and bactericidal compositions, with solid and/or liquid carriers, with or without adjuvants. Conventional carriers or adjuvants can be used.

The fungicidal, fungistatic, bacteriostatic or bactericidal compositions of matter according to the present invention can be used for rendering surgical instruments and the like substantially germ-free and free of fungi. They can be used in households for disinfection and cleansing. They can be used in agriculture for the disinfection of fruit and vegetables prior to packaging. They can be used in agriculture against various fungi afflicting cultivated plants and crops. Other uses will be apparent to those versed in the art.

DESCRIPTION OF THE PREFERRED EMBODIMENTS

The following examples are illustrative of the process and products of the present invention, but are not to be construed in a limitative sense.

EXAMPLE I

Preparation of 4-phenyl-1,2-bis-(trichloromethylthio)urazole

To a solution of 35.4g (0.2 mole) 4-phenyl urazole in 200 ml water was added a solution of 16g (0.4 mole) sodium hydroxide in 20 ml water. A mixture of 74.4g (0.4 mole)trichloromethylsulfenyl chloride and 3g of an emulsifier solution (EXEM 25, consisting of a mixture of alkyl benzene sulfonate and ethoxylated vegetable oil) in 50 ml water was added dropwise to the above basic solution while keeping the reaction mixture at 0° C. The reactants were mixed so that the reaction mixture was kept at a pH greater than 7. The precipitate that formed was filtered and the filter cake was washed with water. After drying and recrystallizing from benzene there was obtained 4-phenyl-1,2-bis-(trichloromethylthio)urazole having a melting point of 175° C.

| Analysis | C | H | Cl | N | S |
|---|---|---|---|---|---|
| Calculated | 25.21 | 1.05 | 44.74 | 8.83 | 13.44 |
| Found | 25.45 | 1.05 | 45.20 | 8.80 | 13.30 |

EXAMPLE 2

Preparation of 4-(3-chlorophenyl)-1,2-bis-(trichloromethylthio)urazole

To a solution of 42.2g (0.2 mole) 4-(3-chlorophenyl) urazole in 200 ml water was added a solution of 16g (0.4 mole) sodium hydroxide in 20 ml water. A mixture of 74.4g (0.4 mole) trichloromethylsulfenyl chloride and 3g of an emulsifier solution (as in example 1) in 50 ml water was added dropwise to the above basic solution while keeping the reaction mixture at 0° C. The reactants were mixed so that the reaction mixture was kept at a pH greater than 7. The precipitate that formed was filtered and the filter cake was washed with water. After drying and recrystallizing from cyclohexane there was obtained 70g (69%) 4-(3-chlorophenyl)-1,2-bis-(trichloromethylthio) urazole having a melting point of 153° C.

| Analysis | C | H | N | Cl | S |
|---|---|---|---|---|---|
| Calculated | 23.48 | 0.78 | 8.22 | 48.72 | 12.52 |
| Found | 23.38 | 1.04 | 8.27 | 47.10 | 12.87 |

EXAMPLE 3

Preparation of 4-(4-chlorophenyl)-1,2-bis-(trichloromethylthio)urazole

To a solution of 42.2g (0.2 mole) 4-(4-chlorophenyl-)urazole in 200 ml water was added a solution of 16g (0.4 mole) sodium hydroxide in 20 ml water. A mixture of 74.4g (0.4 mole) trichloromethylsulfenyl chloride and 3g of an emulsifier solution (as in example 1) in 50 ml water was added dropwise to the above basic solution while keeping the reaction mixture at 0° C. The reactants were mixed so that the reaction mixture was kept at a pH greater than 7. The precipitate that was formed was collected on a filter and the filter cake was washed with water. After drying, triturating with ethyl ether, and recrystallizing from benzene-cyclohexane (1:1, by volume) there was obtained 42g (64%) of 4-(4-chlorophenyl)-1, 2-bis(trichloromethylthio)urazole having a melting point of 169° C.

EXAMPLE 4

Preparation of 4-methyl-1-phenyl-2-(trichloromethylthio)urazole

To a solution of 38.2g (0.2 mole) 4-methyl-1-phenyl urazole in 200 ml water was added a solution of 8g (0.2 mole) sodium hydroxide in 20 ml water. A mixture of 37.2g (0.2 mole) trichloromethylsulfenyl chloride and 3g of an emulsifier solution (as in example 1) in 25 ml water was then added dropwise to the above basic solution while keeping the reaction mixture at 0° C. The reactants were mixed so that the reaction mixture was kept at a pH greater than 7. The precipitate that formed was filtered and the filter cake washed with water. After drying and recrystallizing from benzene there was obtained 67g (99% 4-methyl-1-phenyl-2-(trichloromethylthio)urazole having a melting point of 214° C.

| Analysis | C | H | N | Cl | S |
|---|---|---|---|---|---|
| Calculated | 35.24 | 2.34 | 12.33 | 31.28 | 9.40 |
| Found | 37.90 | 3.66 | 12.74 | 27.95 | 9.21 |

EXAMPLE 5

Preparation of 4-(3,4-dichlorophenyl)-1,2-bis(trichloromethylthio)urazole

To a solution of 24.6g (0.1 mole) 4-(3,4-dichlorophenyl)urazole in 100 ml water was added a solution of 8g (0.2 mole) sodium hydroxide in 10 ml water. A mixture of 37.2g (0.2 mole) trichloromethylsulfenyl chloride and 1.5g of an emulsifier solution (as in example 1) in 25 ml water was added dropwise to the above basic solution while keeping the reaction mixture at 0° C. The precipitate that formed was filtered and the filter cake was washed with water. After drying and recrystallizing from benzene there was obtained 48g (87%) of 4-(3,4-dichlorophenyl)-1,2-bis(trichloromethylthio)urazole having a melting point of 167° C.

| Analysis | C | H | Cl | N | S |
|---|---|---|---|---|---|
| Calculated | 22.02 | 0.55 | 52.11 | 7.71 | 11.78 |
| Found | 22.32 | 0.81 | 52.12 | 7.73 | 12.33 |

EXAMPLE 6

Preparation of
4-methyl-1,2-bis(trichloromethylthio)urazole

To a solution of 23g (0.2 mole) 4-methyl urazole in 200 ml water was added a solution of 16g (0.4 mole) sodium hydroxide in 20 ml water. A mixture of 74.4g (0.4 mole)trichloromethylsulfenyl chloride and 3g of an emulsifier solution (as in example 1) in 50 ml water was then added dropwise to the above basic solution keeping the reaction mixture at 0° C. The reactants were mixed so that the reaction mixture was kept at pH greater than 7. The precipitate that formed was filtered and the filter cake washed with water. After drying, triturating with ethyl ether, and recrystallizing from cyclohexane there was obtained 75g (91%) 4-methyl-1,2-bis-(trichloromethylthioj) urazole having a melting point of 104° C.

| Analysis | C | H | Cl | N | S |
|---|---|---|---|---|---|
| Calculated | 14.48 | 0.74 | 10.14 | 51.45 | 15.46 |
| Found | 14.47 | 0.57 | 10.03 | 48.66 | 15.95 |

Following the procedure of Example 1 but substituting the appropriate haloalkylsulfenyl halide for trichloromethylsulfenyl chloride the following urazoles were prepared:

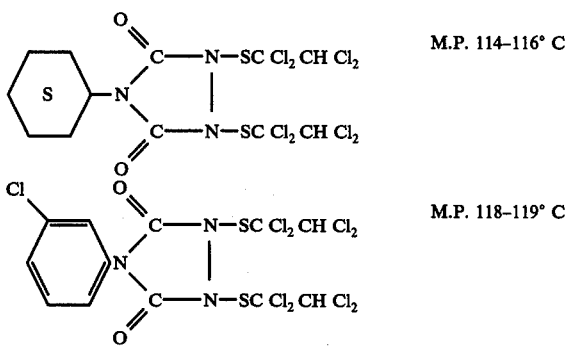

M.P. 114–116° C

M.P. 118–119° C 4-phenyl-1,2-bis-(bromochlorofluoromethylthio)urazole,
4-phenyl-1,2-bis-(bromodichloromethylthio)urazole,
4-phenyl-1,2-bis-(chlorodifluoromethylthio)urazole,
4-phenyl-1,2-bis-(dichloromethylthio)urazole,
4-phenyl-1,2-bis-(fluorodichloromethylthio)urazole,
4-phenyl-1,2-bis-(1-fluoro-1,1,2,2-tetrachloroethylthio)urazole,
4-phenyl-1,2-bis(1,1,2,2-tetrachloroethylthio)urazole,
4-phenyl-1,2-bis-(1,2,2-trichloroethylthio)urazole,
4-phenyl-1,2-bis-(2,2,2-trichloroethylthio)urazole,
4-(3,4-dichlorophenyl)-1,2-bis-(fluorodichloromethylthio)urazole,
4-(3,4-dichlorophenyl)-1,2-bis-(1-fluoro-1,2,2-tetrachloroethylthio)urazole,
4-(3,4-dichlorophenyl)-1,2-bis-(1,1,2,2-tetrachloroethylthio)urazole,
4-(3,4-dichlorophenyl)-1,2-bis-(1,2,2-trichloroethylthio)urazole,
4-methyl-1,2-bis-(fluorodichloromethylthio)urazole,
4-methyl-1,2-bis-(1-fluoro-1,1,2,2-tetrachloroethylthio)urazole,
4-methyl-1,2-bis-(1,1,2,2-tetrachloroethylthio)urazole, and
4-methyl-1,2-bis-(1,2,2-trichloroethylthio)urazole.

Following the same procedure as in example 1, but substituting the appropriate 4-aryl and 4-alkyl urazoles for the 4-phenyl urazoles, there were prepared the following compounds:
4-(4-bromophenyl)-1,2-bis-(trichloromethylthio)urazole,
4-(3-methylphenyl)-1,2-bis-(trichloromethylthio)urazole,
4-(4-chloromethylphenyl)-1,2-bis-(trichloromethylthio)urazole,
4-(4-trifluoromethylphenyl)-1,2-bis-(trichloromethylthio)urazole,
4-(4-methoxyphenyl)-1,2-bis-(trichloromethylthio)urazole,
4-(4-nitrophenyl)-1,2-bis-(trichloromethylthio)urazole,
4-(4-methylthiophenyl)-1,2-bis-(trichloromethylthio)urazole,
4-(2-chloro-4-bromophenyl)-1,2-bis-(trichloromethylthio)urazole,
4-ethyl-1,2-bis-(trichloromethylthio)urazole,
4-propyl-1,2-bis-(trichloromethylthio)urazole,
4-isopropyl-1,2-bis-(trichloromethylthio)urazole,
4-cyclopropyl-1,2-bis-(trichloromethylthio)urazole,
4-butyl-1,2-bis-(trichloromethylthio)urazole,
4-cyclobutyl-1,2-bis-(trichloromethylthio)urazole,
4-octyl-1,2-bis-(trichloromethylthio)urazole,
4-chloromethyl-1,2-bis-(trichloromethylthio)urazole, and
4-benzyl-1,2-bis-(trichloromethylthio)urazole,
4-cyclohexyl-1,2-bis-(trichloromethylthio)urazole.

EXAMPLE 7

Preparation of
4-phenyl-1-methyl-2-(trichloromethylthio)urazole

To a solution of 38.2g (0.2 mole) 4-phenyl-1-methyl urazole in 200 ml water was added a solution of 8g (0.2 mole) sodium hydroxide in 20 ml water. A mixture of 37.2g (0.2 mole) trichloromethylsulfenyl chloride and 3g of an emulsifier solution (as in example 1) in 25 ml water was then added dropwise to the above basic solution while keeping the reaction mixture at 0° C. The reactants were mixed so that the reaction mixture was kept at a pH greater than 7. The precipitate that formed was filtered and the filter cake washed with water. After drying and recrystallizing from benzene-cyclohexane (1:1, by volume) there was obtained 65g (91%) 4-phenyl-1-methyl-2-(trichloromethylthio) urazole having a melting point of 154° C.

Following the procedure of Example 7 but substituting the appropriate urazoles for the 4-phenyl-1-methyl urazole there are prepared the following compounds:
1,4-dimethyl-2-(trichloromethylthio)urazole,
4-benzyl-1-isopropyl-2-(trichloromethylthio)urazole,
1,4-diphenyl-2-(trichloromethylthio)urazole,
4-(3,4-dichlorophenyl)-1-butyl-2-(trichloromethylthio)urazole.

EXAMPLE 8

Several compounds were tested for their fungicidal activity against Pencillium spores using a modified Agar plate method as follows:

In a petri dish were placed 15 ml of a Malt Agar extract and 1 ml of a suspension of Pencillium spores at a constant concentration of 40 KU(filter 42) diluted to 1:10$^4$. The test materials were added to the petri dishes as 1 ml water solutions containing two percent acetone and 0.3% of an emulsifier (see example 1). Treatment I consisted of 1 ml of a water solution of the test compound at various concentrations. Treatment II consisted of 1 ml of a solution of Captan in water at a concentration of 200 ppm as a standard reference fungicide. Treatment III consisted of 1 ml of water as a control. The results were determined by observation of the number of colonies using a colony counter and expressed in LD$_{50}$ values (see Table 1). Treatment II gave total inhibition.

Similar tests were conducted against Botrytis Cinerea and Aspergillus Niger. The results are all tabulated in Table 1.

TABLE 1

| R | R' | R" | LD$_{50}$(ppm) Penicillium Chrysogenom | LD$_{50}$(ppm) Botrytis Cinerea | LD$_{50}$(ppm) Aspergillus |
|---|---|---|---|---|---|
| CH$_3$ | CCl$_3$ | C$_6$H$_5$ | 5.0 | 18.0 | 10 |
| C$_6$H$_5$ | CCl$_3$ | CH$_3$ | 3.0 | 22.0 | 16 |
| CH$_3$ | CCl$_3$ | SCCl$_3$ | 16 | 17 | 15.0 |
| n-C$_4$H$_9$ | CCl$_3$ | SCCl$_3$ | 20 | 27 | 17 |
| C$_6$H$_5$ | CCl$_3$ | SCCl$_3$ | 8 | 120 | 56 |
| 3-Cl-C$_6$H$_4$ | CCl$_3$ | SCCl$_3$ | 14 | — | 16 |
| 4-ClC$_6$H$_4$ | CCl$_3$ | SCCl$_3$ | 19 | 80 | 54 |
| 3,4-Cl$_2$C$_6$H$_3$ | CCl$_3$ | SCCl$_3$ | 19 | 170 | 110 |
| C$_6$H$_5$ | CCl$_2$CHCl$_2$ | SCCl$_2$CHCl$_2$ | 2.5 | — | — |
| 3-ClC$_6$H$_4$ | CCl$_2$CHCl$_2$ | SCCl$_2$CHCl$_2$ | 6.2 | — | — |
| CAPTAN | | | 1.4 | | |

We claim:

1. A compound having the formula wherein R is alkyl of 1-12 carbon atoms, cycloalkyl having 3-6 carbon atoms, lower mono haloalkyl, benzyl, phenylethyl and phenyl, optionally substituted by 1-3 halogens, nitro, chloromethyl, trifluoromethyl, lower alkyl, lower alkoxy or lower alkylthio groups;
    R' is haloalkyl having 1 to 2 carbon atoms and at least 2 halogen substituents;
    R" is R or — SR'; and
    X and Y are independently oxygen or sulfur.

2. A compound in accordance with claim 1 wherein R" is — SR'.

3. A compound in accordance with claim 1 wherein R' is trichloromethyl.

4. A compound in accordance with claim 1 wherein X and Y are oxygen.

5. A compound in accordance with claim 1 wherein R is selected from the group consisting of lower alkyl, cyclohexyl and phenyl optionally substituted by 1 to 2 halogens.

6. A compound in accordance with claim 1; 4-(3,4-dichlorophenyl)-1,2-bis-(trichloromethylthio)urazole.

7. A compound in accordance with claim 1; 4-(4-chlorophenyl)-1,2-bis-(trichloromethylthio)urazole.

8. A compound in accordance with claim 1; 4-(3-chlorophenyl)-1,2-bis-(trichloromethylthio)urazole.

9. A compound in accordance with claim 1; 4-methyl-1-phenyl-2-(trichloromethylthio)urazole.

10. A compound in accordance with claim 1; 4-methyl-1,2-bis-(trichloromethylthio)urazole.

11. A process for preparing compounds having the formula:

wherein R is alkyl of 1-12 carbon atoms, cycloalkyl having 3-6 carbon atoms, lower mono haloalkyl, benzyl, phenylethyl and phenyl, optionally substituted by 1-3 halogens, nitro, chloromethyl, trifluoromethyl, lower alkyl, lower alkoxy or lower akylthio groups;
    R' is haloalkyl having 1 to 2 carbon atoms and at least 2 halogen substituents;
    R" is R or SR'; and
    X and Y are independently oxygen or sulfur, which comprises a 4-substituted urazole or thiourazole in an alkaline media with a haloalkylsulfenyl halide having 1 to 2 carbon atoms and at least 2 halogen atoms attached to the carbon atoms at a temperature between −10° to 30° C, maintaining the pH at a value greater than 7 and separating the resultant 4-substituted-1-(haloalkylthio)- or 1,2-bis-(haloalkylthio)urazole or thiourazole.

12. A biocidal composition containing in a biologically effective amount one or more compounds of the formula:

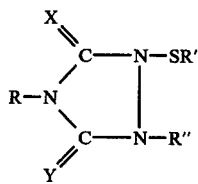

wherein R is alkyl of 1-12 carbon atoms, cycloalkyl having 3-6 carbon atoms, lower mono haloalkyl, benzyl, phenylethyl and phenyl, optionally substituted by 1-3 halogens, nitro, chloromethyl, trifluoromethyl, lower alkyl, lower alkoxy or lower alkylthio groups;

R' is haloalkyl having 1 to 2 carbon atoms and at least 2 halogen substituents;

R" is R — or SR'; and

X and Y are independently oxygen or sulfur; and a solid or liquid carrier.

13. Compositions according to claim 12, wherein R' is trichloromethyl.

14. Compositions according to claim 12, wherein X and Y are oxygen.

15. A method for controlling fungi which comprises applying to the fungus infested material or plant a composition according to claim 12.

* * * * *